United States Patent [19]

Wiley

[11] Patent Number: 5,203,788

[45] Date of Patent: * Apr. 20, 1993

[54] MICROMOTOR ACTUATED ADJUSTABLE FOCUS LENS

[76] Inventor: Robert G. Wiley, 4545 Brookside Rd., Toledo, Ohio 43615

[*] Notice: The portion of the term of this patent subsequent to Apr. 28, 2009 has been disclaimed.

[21] Appl. No.: 669,499

[22] Filed: Mar. 14, 1991

[51] Int. Cl.⁵ ............................................. A61F 2/16
[52] U.S. Cl. ...................................................... 623/6
[58] Field of Search ..................... 623/6; 350/419, 423

[56]  References Cited

U.S. PATENT DOCUMENTS

| | | |
|---|---|---|
| 4,277,852 | 7/1981 | Poler . |
| 4,373,218 | 2/1983 | Schachar . |
| 4,444,471 | 4/1984 | Ford, Jr. et al. ............... 350/419 |
| 4,512,039 | 4/1985 | Lieberman . |
| 4,514,048 | 4/1985 | Rogers ............................ 350/423 |
| 4,564,267 | 1/1986 | Nishimoto . |
| 4,575,373 | 3/1986 | Johnson . |
| 4,601,545 | 7/1986 | Kern . |
| 4,787,903 | 11/1988 | Grendahl . |
| 4,816,031 | 3/1989 | Pfoff ................................. 623/6 |

*Primary Examiner*—Randy C. Shay
*Attorney, Agent, or Firm*—Marshall & Melhorn

[57] ABSTRACT

An adjustable focus lens apparatus includes a transparent lens body having a periphery, and a relatively rigid outer ring extending about the periphery of the lens body and a plurality of micromotor devices spaced equally about and coupled between the ring and the periphery. Each of the micromotor devices is responsive to an externally generated control signal for selectively changing the circumference and/or axial position of an associated portion of the periphery to adjust the lens for power and astigmatism correction. In several embodiments, the periphery includes an inner ring coupled to the outer ring by the micromotor devices. In another embodiment, the ring is formed of segments and the micromotor devices are included in overlapping portions of the segments.

7 Claims, 4 Drawing Sheets

MICROMOTOR ACTUATED ADJUSTABLE FOCUS LENS

BACKGROUND OF THE INVENTION

The present invention relates generally to an adjustable focus lens and, in particular, to an intraocular lens system capable of varying its power and providing astigmatism correction after implantation into the eye through the aid of externally controlled micromotors.

The lens of the human eye is located centrally behind the pupil and is protected by the cornea. In the normal eye, the lens is clear and is substantially symmetrical, with opposed convex surfaces defining generally spherical sections. The lens and the cornea cooperate to focus light on the retina. The retina in turn cooperates with the nerves and the brain, so that light impinging on the retina is perceived as an image.

The light refraction which takes place in the cornea and the lens translates into an optical correction of about 60 diopters, with the cornea accounting for about 40 diopters and the lens accounting for about 20 diopters. Other refracting structures also are present in the eye, but are disregarded to simply the subject explanation.

A cataract is a condition where the normally clear lens of the eye becomes progressively opaque. This opacification typically occurs over an extended period of time, and the amount of light which passes through the lens decreases with increasing degrees of opacity. As the ability of the cataract lens to transmit light decreases, the ability of the eye to perceive images also decreases. Blindness ultimately can result. Since there are no known methods for eliminating the opacity of a cataract lens, it generally is necessary to surgically remove the opaque lens to permit the unobstructed passage of light through the pupil to the retina. The cataract lens is removed through a generally horizontal incision made at the superior part of the juncture where the cornea and sclera meet.

Once the lens has been surgically removed, light can be readily transmitted through the pupil and toward the retina. As noted above, the lens of the eye performs a significant light focusing function. Consequently, with the lens removed, the optical system of the eye is left about 20 diopters "short", and light is no longer properly focused on the retina. Eyeglasses, contact lenses and intraocular lenses are the three types of optical aids that commonly may be employed after cataract surgery to refocus the light on the retina.

Eyeglasses include lenses which are spaced from the cornea of the eye. The air space between the lens and the cornea causes an image magnification of more than 7%. Unfortunately, the brain cannot assimilate this magnification in one eye, and as a result an object appears double. This is a particular problem if the individual had only one cataract eye. Eyeglasses also substantially limit peripheral vision.

Contact lenses rest directly on the cornea of the eye, thus eliminating the air space. As a result, there is a much smaller image magnification with contact lenses than there is with eyeglasses, and the brain typically can fuse the images perceived by an eye with a contact lens and one without. Contact lenses, however, are less than perfect. For example, contact lenses are quite fragile and can be easily displaced from their proper position on the cornea. Additionally, the lenses must be periodically replaced because of protein build-up on the surface of the lens which can cause conjunctivitis. Furthermore, many of the elderly people who require cataract operations do not have the required hand coordination to properly remove or insert the lens.

Intraocular lenses first because available as optical aids to replace removed cataract lenses in the 1950's. These lenses are placed in the eye, and thus closely simulate the optics of the natural lens which they are replacing. Unlike eyeglasses, there is virtually no image distortion with a properly made and placed intraocular lens. Also, unlike contact lenses, there is no protein build-up on the intraocular lenses and the lenses require no care by the patient.

To place the lens in the eye, the surgeon ordinarily makes an incision or opening in the sclera and cornea to allow the insertion of the lens into the eye. Normally, the stabilizing loops of the attachment members of the lens are flexible and can be bent, if necessary, to pass through the opening. Accordingly, the minimum length of opening which must be made and is ordinarily determined by the diameter of the substantially rigid lens body, or optic, usually having a circular periphery. It is, of course, desirable to make the opening into the eye as small as possible to minimize the risk of damage to the eye. In the past few years, some lenses have been made of flexible material like silicone that can be folded so as to go into the eye through a smaller opening.

The current practice in the implantation of intraocular lenses is to replace a normal crystalline human lens of the eye removed at the time of surgery, such as in cataract surgery, with an intraocular lens such as an anterior chamber lens or posterior chamber lens formed of appropriate biocompatible material such as PMMA (polymethyl methacrylate) material. However, one of the present problems with intraocular lenses is that it is necessary to decide on the power of the lens preoperatively. This can be accomplished, for example, by performing an ultrasound scan and/or evaluating the patient's refraction preoperatively and then making a clinical estimate of the proper power of the lens in order to determine proper refraction of the eye. However, even with the best medical techniques and sophisticated optical instruments available, ophthalmologists have never been able to correct for accommodation which is the ability to change the focus of vision from distance to near vision and there is no lens system that can be adjusted after implantation for even minor changes in spherical or astigmatic power. Thus, most patients, following routine lens implantation, require the use of glasses for precisely focused distance and near vision.

The prior art intraocular lens typically is either of plano-convex construction or double convex construction, with each curved surface defining a spherical section. The lens is placed in the eye through the same incision which is made to remove the cataract lens. As noted above, this incision typically is made along the superior part of the eye near the juncture of the cornea and the sclera. About one third of all postoperative patients will have significant astigmatism and, approximately one third will need a spherical adjustment in their postoperative glasses to see clearly. In virtually all instances, the surgery itself induces astigmatism which fluctuates significantly during the first few weeks, or even months, after the surgery.

Postoperative induced astigmatism is attributable to the healing characteristics of the eye adjacent the incision through which the cataract lens is removed and the intraocular lens is inserted. More particularly, the incision in the eye tends to heal slowly. The incision in the eye may take eight weeks to a year to properly heal. During the period when the eye is healing, the wound area tends to spread and thus a cornea that may have been spherical before surgery is made other than spherical. Since the incision is generally horizontally aligned, the spreading is generally along the vertical meridian. Initially, after the surgery, the cornea is relatively steep in the vertical meridian. As the eye heals, the cornea becomes relatively flat in the vertical meridian. Consequently, the optical system of the eye, which may previously have been spherical, becomes "toric" with the vertical meridian of the optical system providing a different optical power than the horizontal meridian. This non-spherical configuration of the optic system is generally referred to as "astigmatism".

The degree of this induced astigmatism varies according to the type of incision made, the presence or absence of sutures or the number and type of sutures used, the technical skill and care employed by the surgeon, and the physical attributes of the eye. For example, the use of a fine nylon suturing material typically results in a smaller deviation from sphericity than the use of silk or absorbable sutures. Generally, the induced astigmatism varies from 0.5 to 5 diopters. The initial postoperative astigmatism is generally caused by the steepening of the vertical meridian. Late astigmatism is caused by the flattening of the vertical meridian of the cornea. The orientation and amount of postoperative astigmatism are, in most cases, not accurately predictable. Postoperative astigmatism typically is corrected by prescription eyeglasses which need to be changed periodically as the eye heals.

In some cases, despite the best efforts of the ophthalmologist, the lens surgically placed in the patient's eye does not provide good distance visual acuity due to spherical miscalculations and due to the changing astigmatic requirements. Since the surgery itself can cause significant change in the amount and axis of the astigmatism present after cataract surgery, the exact amount and axis of astigmatism can not be accurately determined until sometime, usually several weeks or months, after the surgery. Since the old intraocular lens can not be readily removed and a new intraocular lens with a different power surgically installed without unduly jeopardizing the patient's vision, the patient must rely on spectacles to provide accurately focused visual acuity. In other words, although the need to wear heavy, bulky, higher power spectacles is eliminated, the patient nevertheless usually must wear spectacles for best focused vision.

Several attempts have been made to provide an intraocular lens which corrects for the astigmatism expected after surgery or can be varied in spherical power after implantation. U.S. Pat. No. 4,575,373 discloses a laser adjustable intraocular lens which utilizes a laser to alter, in situ, the power of an implanted intraocular lens. The outer ring of the lens is manufactured of a non-toxic heat shrinkable colored plastic material to permit selective absorption of laser energy, thereby causing the shape of the lens to change increasing the power irreversibly.

U.S. Pat. No. 4,816,031 discloses an intraocular lens system including a PMMA lens implant, a second soft and pliable lens positioned thereover, and electromechanical circuitry for regulating the distance between the two lenses, thereby providing for adjustment of the focal point of the lens system.

U.S. Pat. No. 4,512,039 discloses an intraocular lens for offsetting postoperative astigmatism having the finally placed vertical meridian optically weaker than the horizontal meridian. Proper placement is ensured by disposing the haptics along the vertical meridian.

U.S. Pat. No. 4,277,852 discloses an intraocular lens with astigmatism correction combined with a supporting mount or haptic structure to assure correct optical orientation of the implant.

Several attempts have been made to provide a variable power intraocular lens, which power varies according to an application of a force external to the lens, for correcting the astigmatism expected after surgery. U.S. Pat. No. 4,787,903 discloses an intraocular lens including an annular Fresnel (prism) lens, made of a high index of refraction material such as polymethylmethacrylate. A composite material overlays the Fresnel elements to provide a smooth external surface and is made of a suitable material, for example, crystalline lattice or liquid crystal material, which changes the index of refraction when excited with electrical power or radiant energy. The lens carries a complementary loop or other energy pick-up device, for receiving the power from an electric field generated by an external power source feeding a coupling loop. The coupling loop can be carried in an eyeglass frame, implanted about the eye socket or positioned by the lens wearer or an ophthalmologist. It is stated in the patent specification that some overlay materials can be switchable between more than two states, each with a different index of refraction, while other materials will provide a continuously variable index of refraction which may be stable or may return to an initial value when the energy is removed. However, such materials are not identified in the patent.

U.S. Pat. No. 4,601,545 discloses a variable power lens system including an optically active molecular material such as liquid crystals. A variable gradient index of refraction is achieved by applying a controlled stimulus field, such as a geometrically configured matrix of electrical voltages, to the lens. A corresponding matrix of horizontal and vertical conductors applies the electrostatic field produced by the applied voltage to be selectively controlled at discrete points so that a gradient index of refraction is produced.

U.S. Pat. No. 4,564,267 discloses a variable focal length lens which can be electrically controlled by applying an electric field to a compound lens including at least one lens formed of electrooptic crystals. The electrooptic crystals are juxtaposed between first and second transparent electrode plates each comprising a plurality of concentric annular transparent electrodes. A power source connected to the electrodes generates an electric field across the crystals creating a refracting index distribution having a lens action. The electric field effectuates a change in the focal length of the lens which varies according to the potential imparted.

U.S. Pat. No. 4,373,218 discloses a variable power intraocular lens including a fluid expandable sac for containing a liquid crystal material that is used in combination with an electrode and a microprocessor for changing the index of refraction of the lens. An electrode is located in a ciliary body to provide an input signal that is proportional to a desired accommodation to a microprocessor which can be implanted into a sclera of a human eye. The microprocessor produces a potential across the liquid crystal material to control the index of refraction to obtain the desired accommodation based upon the relative position of the eyes. The voltage output of the microprocessor is applied to electrodes which can be a thin transparent material forming a coating on the interior of the fluid expandable sac.

SUMMARY OF THE INVENTION

The present invention concerns an adjustable focus lens which can be formed as an intraocular lens implanted in the human eye. The lens apparatus includes a transparent lens body having a periphery; a mounting ring extending about at least a portion of the periphery of the lens body; and a plurality of micromotor means spaced equally about and coupled between the ring and the periphery of the lens body. Each of the micromotor means is responsive to an external control signal for selective action to change position and/or the diameter and/or circumference of an associated portion of the lens body periphery for power and astigmatism correction. Power to operate the micromotors can be supplied from an external source and/or stored when the lens apparatus is implanted for later use.

In one embodiment, the lens apparatus includes an expandable and contractible inner ring and a relatively rigid outer ring, the micromotor means being attached to the outer ring and adjustably engaging the inner ring. The micromotor means can be formed as a tuning fork having a pair of generally parallel prongs extending on either side of the inner ring and connected to a base attached to the outer ring. The inner ring has a pair of flanges formed thereon and facing surfaces of the prongs have grooves formed therein for releasably retaining the flanges. The micromotor means also can include a linear positioning device connected between the base of the tuning fork and the inner ring. Power for the micromotor means can be provided from an external source which can be ultrasound, static electricity, magnetic field, laser beam, etc. Power for the micromotor means also can be stored, as potential energy for example, in the micromotor means before implantation for later use.

In another embodiment, the mounting ring is formed of a plurality of segments and the micromotor means controls overlapping portions of the segments wherein facing surfaces of the overlapping portions have cooperating grooves formed therein. The lens body has a hollow edge portion formed at the periphery thereof and the overlapping portions extend through the hollow edge portion. The micromotor means acts to change the circumference of the ring thereby changing the configuration of the lens body.

In other embodiments, the micromotor means can include a fluid powered piston and cylinder system, a helical groove or thread and cooperating nut system, or a track and motive means system coupled between inner and outer rings. These systems permit relative axial and/or radial movement between adjacent portions of the two rings thereby changing the position or configuration of the lens body in the eye.

In an intraocular lens application, the postoperative vision of the lens implant recipient may be repeatably corrected or adjusted to perfect or near perfect vision. The changed power and/or astigmatism correction of the lens remains stable until such time the implant recipient needs to have the external force field applied to correct a deviation from perfect vision caused by other sources (such as the changes in astigmatism common in the healing process) thus eliminating the need for changes in glasses to keep the eye in good focus. Furthermore, due to the passive restraint system in place, the lens according to the present invention is stable, retaining the focus and/or astigmatism correction after the external force field has been removed. Such lens does not require a continuous power source, nor a power source being coupled to the lens material by circuitry and a matrix of electrodes, nor power coupling loops to supply continuous power to the lens. The lens can be easily adjustable: adding or subtracting spherical lens power or adding or subtracting astigmatic lens power thus fine tuning the lens focus as needed as often as necessary over the life of the patient.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
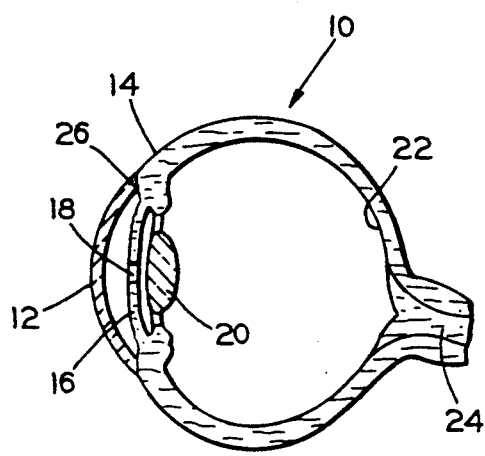
FIG. 1 is a cross-sectional side elevation view of a normal human eye prior to removal of the natural lens.

Referring to the FIG. 1, there is illustrated a normal human eye generally indicated by the reference numeral 10. The eye 10 includes a cornea 12 covering an opening in a generally spherical sclera 14. Positioned interiorly of the cornea 12 in the opening in the sclera 14 is an iris 16 having a pupil 18. Positioned behind the pupil 18 is a lens 20 which focuses entering light onto a retina 22 on the interior surface of the eye, the retina being connected to the brain (not shown) by an optic nerve 24. The lens 20 is located centrally behind the pupil 18 and is protected by the cornea 12. In the normal eye 10, the lens 20 is clear and is substantially symmetrical, with opposed convex surfaces defining generally spherical sections. The lens 20 and the cornea 12 cooperate to focus incoming light on the retina 22. The retina 22 in turn cooperates with the optic nerve 24 and the brain, so that light impinging on the retina 22 is perceived as an image.

The light refraction which takes place in the cornea 12 and the lens 20 translates into an optical correction of about sixty diopters, with the cornea 12 accounting for about forty diopters and the lens 20 accounting for about twenty diopters. Other refracting structures also are present in the eye 10, but are disregarded here to simplify the explanation.

A cataract is a condition where the normally clear natural lens 20 of the eye 10 becomes progressively opaque. This opacification typically occurs over an extended period of time, and the amount of light which passes through the lens 20 decreases with increasing degrees of opacity. As the ability of the cataract lens 20 to transmit light decreases, the ability of the eye 10 to perceive to images also decreases. Ultimately, blindness can result. Since there are no known methods for eliminating the opacity of a cataract lens 20, it generally is necessary to surgically remove the opaque lens 20 to permit the unobstructed passage of light through the pupil 18 to the retina 22. The cataract lens 20 is removed through a generally horizontal incision made at the superior part of a juncture 26 where the cornea 12 and the sclera 14 meet.

Figure 2:
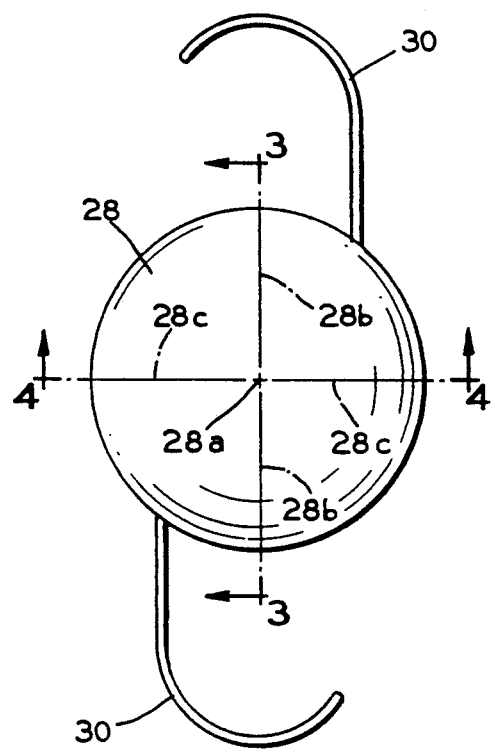
FIG. 2 is a front elevation view of a typical prior art intraocular lens.

Once the cataractous lens 20 has been surgically removed, light can be readily transmitted through the pupil 18 and toward the retina 22. However, the lens 20 performs a significant light focusing function. Consequently, with the lens 20 removed, the optical system of the eye is left about twenty diopters "short", and light is no longer properly focused on the retina 22. When a lens 20 is removed to eliminate cataracts, it must be replaced by an artificial lens. An intraocular lens, such as a prior art intraocular lens 28 shown in the FIG. 2, is routinely employed to refocus the light on the retina 22.

Figure 5:
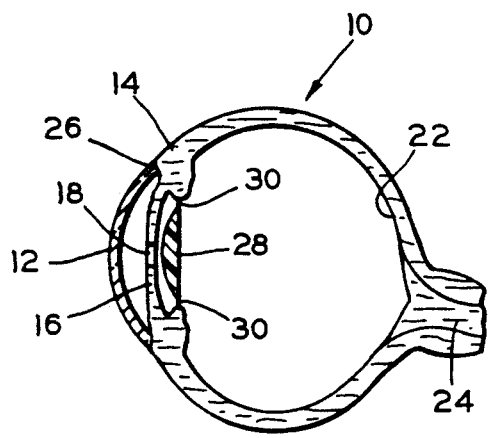
FIG. 5 is a cross-sectional side elevation view of the human eye shown in the FIG. 1 after the insertion of the intraocular lens shown in the FIG. 2.

The intraocular lens 28 can be constructed of any biologically inert, transparent material suitable for optical correction such as, for example, silicone. The lens 28 is a section of a sphere, generally circular as viewed from the front with a diameter of approximately six millimeters. A pair of haptics 30 function as legs or stabilizing loops which support the lens 28 in the proper position in the posterior chamber of the eye 10 (FIG. 5). Each haptic 30 extends approximately four millimeters from a straight end attached to a periphery of the lens 28 to a curved end to be attached to the eye. Thus, the total width of the lens 28 and the haptics 30 is approximately fourteen millimeters.

The intraocular lens 28 is inserted behind the iris 16 as illustrated in the FIG. 5. This type of lens is referred to as a posterior chamber lens, the latest and most popular of the many designs of intraocular lenses.

It should be understood that the prior art lens 28 can be manufactured for positions in the eye other than the posterior chamber. For example, the lens 28 can be placed in the anterior chamber, the area between the cornea 12 and the iris 16. However, such positioning is sometimes considered undesirable because positioning the lens very close to the cornea may result in traumatization of the endothelium of the cornea.

A problem associated with the proper implantation of an intraocular lens is the accurate postoperative determination of the exact prescriptive or refracting power of the lens to be placed in the eye of the patient. The ophthalmologist or optometrist can, for example, attempt to estimate the prescriptive power of the natural lens 20 of the patient and, through the use of various measuring devices, e.g. ultrasound, measure the depth and diameter of the eye 10. These measurements in conjunction with clinical experience permit the ophthalmologist or optometrist to relatively accurately determine the proper refraction or power of the intraocular lens 28 to be implanted.

In some cases however, despite the best efforts of the ophthalmologist or optometrist, the lens surgically placed in the eye is not the correct dioptric power and the patient does not obtain good unaided visual acuity. During the postoperative healing period, the patient has a variable amount of astigmatism, a refracting defect which prevents focusing of sharp distinct images. Some astigmatism present after cataract surgery is due to the surgical incision and changes in corneal curvature as a consequence of the healing of the incision.

Figure 3:
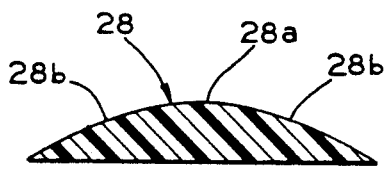
FIG. 3 is a cross-sectional view of the lens shown in the FIG. 2 taken along the line 3—3 on the vertical meridian.
Figure 4:
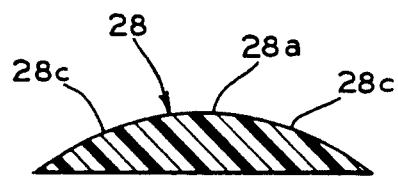
FIG. 4 is a cross-sectional view of the lens shown in the FIG. 2 taken along the line 4—4 on the horizontal meridian.

The curvature in the lens 28 can be formed asymmetrically such that a vertical meridian, along a cross section line 3—3 as illustrated in the FIG. 3, is optically weaker (longer diameter for less curvature) than an horizontal meridian along a cross section line 4—4 as illustrated in the FIG. 4. The thickness of the lens 28 at a center 28a remains constant. Thus, the difference in the respective optical strengths of vertical and horizontal meridians is created by different structural contours (such as different radii of curvature), 28b and 28c, in the vertical and horizontal meridians respectively resulting in different light refracting characteristics. Thus, the lens 28 defines a section of a sphere. In order to properly align the lens 28 at the time of insertion in the eye, the haptics 30 are offset from and extend generally parallel to the vertical meridian. Thus, as explained above, the prior art intraocular lens 28 has a fixed correction and angle for astigmatic power as well as a fixed spherical power.

Figure 6:
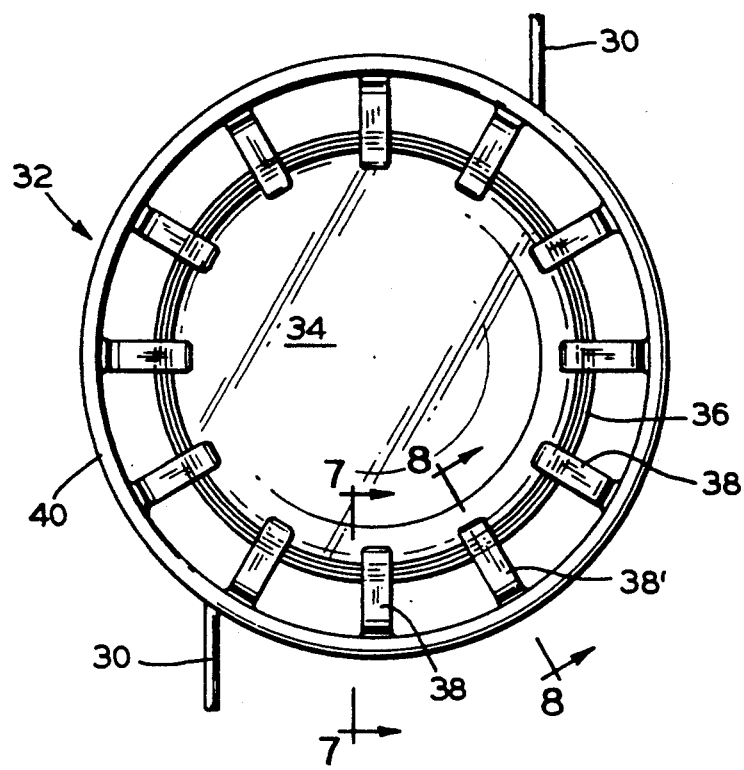
FIG. 6 is a front elevation view of an intraocular lens apparatus in accordance with the present invention.
Figure 7:
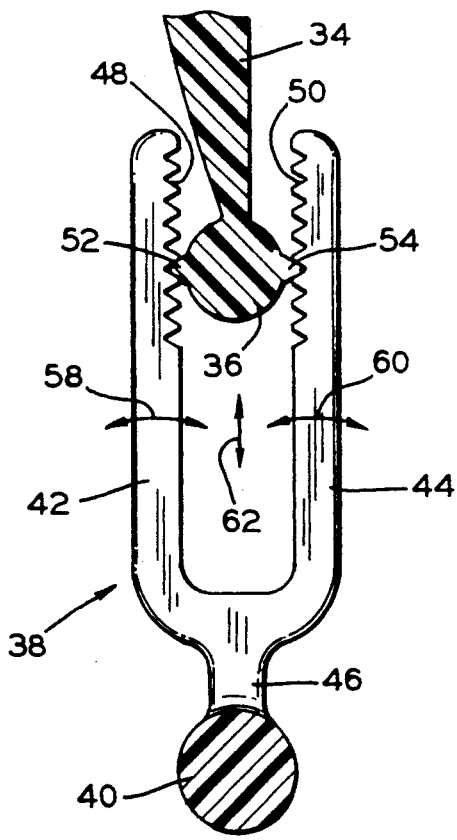
FIG. 7 is an enlarged cross-sectional view of a portion of the lens apparatus shown in the FIG. 6 taken along the line 7—7.
Figure 8:
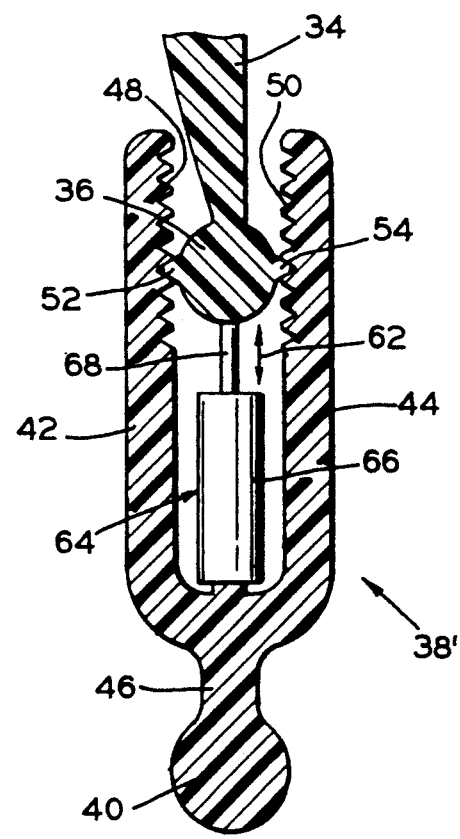
FIG. 8 is an enlarged cross-sectional view of a portion of the lens apparatus shown in the FIG. 6 taken along the line 8—8.

In the FIGS. 6-8, there is shown a micromotor actuated variable focus intraocular lens apparatus according to the present invention generally indicated by a reference numeral 32, which lens is provided with means for selectively changing the spherical power of the lens and means for selectively providing correction for astigmatism. The lens apparatus 32 includes a central lens body 34 formed of a transparent flexible material, such as a silicone or the like. The lens body 34 is generally disc-shaped and has an anterior convex surface adapted to be centered in the pupil of an eye and planar rear surface. However, the anterior and rear surfaces can be any desired combination of concave, planar and convex. An inner ring 36 is attached about a periphery of the lens body 34 by any suitable means, such as being molded integral therewith as shown in the FIG. 7. The inner ring or rings 36 can be formed of any suitable elastomeric material to provide for appropriate expansion and contraction of its periphery with the abilities to become oval, segmented or wave like and the peripheral circumference depending upon the orientation of the micromotor.

The ring 36 is retained by a plurality of spaced micromotors 38 extending radially inwardly toward the center of the lens body 34. The micromotors 38 each have an inner end for retaining the inner ring 36 and an outer end attached to an outer ring 40 which extends concentrically about the inner ring 36. The outer supporting or mounting ring 40 is made from a rigid plastic or other material and provides a fixed support for the micromotors 38 and the lens body 34. A pair of haptics 30 can be attached to the ring 40 to support the lens apparatus 32 in the proper position in the eye.

As shown in the FIG. 7, each of the micromotors 38 can be formed as a tuning fork having a pair of spaced apart generally parallel prongs or legs 42 and 44 branching from a base or handle 46 attached to the outer ring 40. Facing surfaces of the prongs 42 and 44 have grooves or teeth 48 and 50 respectively formed therein. The grooves 48 and 50 cooperate with a pair of opposed flanges 52 and 54 respectively formed on the inner ring 36 to retain the adjacent portion of the lens body 34 and the inner ring 36 a selected distance from the outer ring 40.

If the inner ring 36 is expanded and increased in diameter, the lens body 34 will tend to become less curved and the power of the lens assembly 32 will be reduced. If the inner ring 36 is contracted and reduced in diameter, the lens body 34 will tend to become more curved and the power of the lens assembly 32 will be increased. The micromotors 38 cooperate with the inner ring 36 to provide selective adjustment of the power of the lens from outside the eye. Each of the micromotors 38 can be powered by a control signal from an external energy source, not shown, such as a source of ultrasonic energy at a predetermined controlled frequency and/or amplitude which tends to vibrate the prongs 42 and 44, oscillating them in the direction of the double headed arrows 58 and 60 respectively. This produces a wave action that can cause selective movement of the flanges 52 and 54 in the direction of the double headed arrows 58 and 60 respectively. As each of the prongs 42 and 44 moves horizontally, the associated flanges 52 and 54 will disengage from the grooves 48 and 50 respectively and then reengage in a different groove further away or closer to the outer ring 40 depending on the externally controlled frequency and thus the propelling wave action generated longitudinally along the prongs 42 and 44. The micromotor 38 can be responsive to different amplitudes of ultrasonic energy: it can be responsive to ultrasonic energy at a first predetermined frequency for contracting and a second predetermined frequency for expanding the inner ring 36.

There is illustrated in the FIG. 8 an alternate embodiment of the micromotor 38. A micromotor 38' is formed similarly to the micromotor 38, but includes a linear positioning device 64 located between the prongs 42 and 44. The positioning device 64 has a body 66 attached at one end to the base 46. A rod 68 extends from the opposite end of the body 66 and has a free end attached to the inner ring 36. The linear positioning device is responsive to a control signal from an external source of energy (not shown) for extending and retracting the rod 68 thereby moving the ring 36 in the direction of the arrow 62 to change the shape of the lens body 34. The source of energy can be ultrasonic as discussed above. The source of energy can be electromagnetic (laser beam, radio waves, etc.). In either case, conventional devices are known for converting such energy into the linear motion 62.

If all of the micromotors 38 and 38' are operated to maintain the inner ring 36 in a circular configuration, only the power of the lens assembly 32 will be changed. If individual ones of the micromotors are operated to change the shape of associated segments of the lens body 34, a selective correction for astigmatism can be made. One micromotor can be actuated to correct for irregular astigmatism and two opposing micromotors can be actuated to correct for regular astigmatism. Each of the micromotors 38 and 38' can be responsive to a different frequency for selective actuation or each micromotor can be selectively activated by external selective stimulation.

Figure 9:
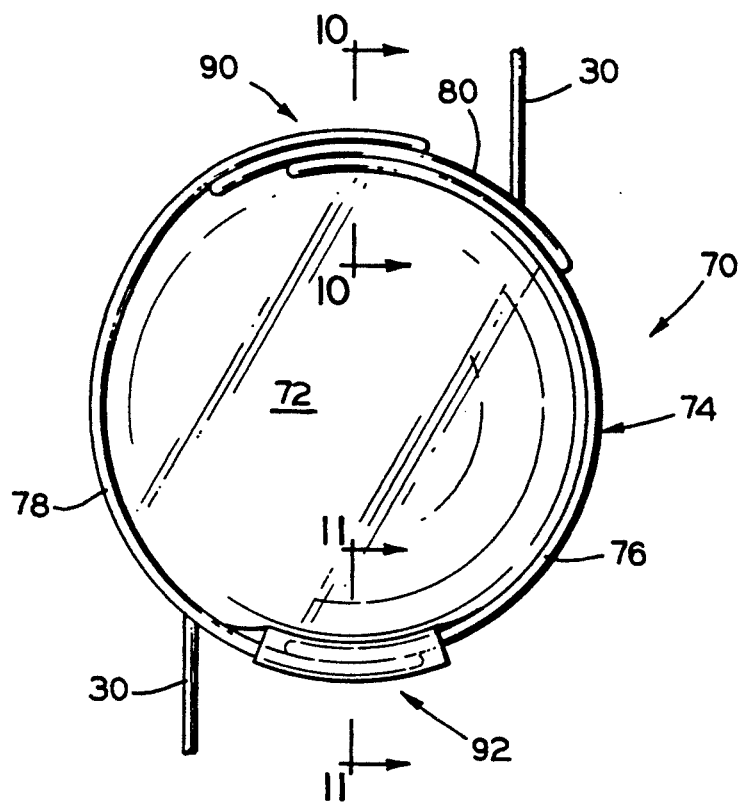
FIG. 9 is a front elevation view of an alternate embodiment of the intraocular lens apparatus according to the present invention.
Figure 10:
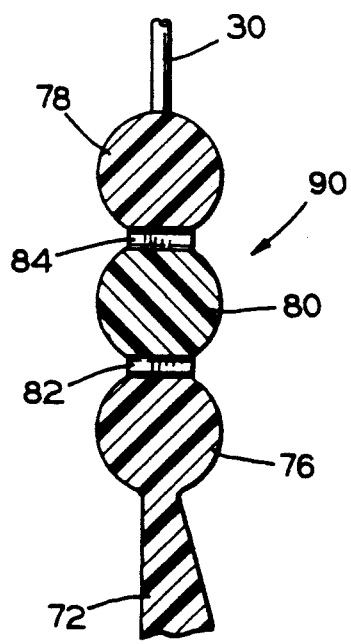
FIG. 10 is an enlarged cross-sectional view of a portion of the lens apparatus shown in the FIG. 9 taken along the line 10—10.
Figure 11:
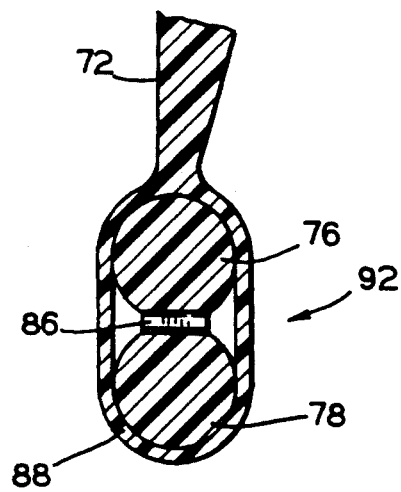
FIG. 11 is an enlarged cross-sectional view of a portion of the lens apparatus shown in the FIG. 9 taken along the line 11—11.

In the FIGS. 9-11 there is illustrated an alternate embodiment of the present invention. A lens apparatus 70 has a flexible central lens body 72 attached at a periphery thereof to a relatively rigid mounting or supporting ring 74 formed of a plurality of overlapping curved segments. Although only three segments 76, 78 and so are shown, the ring 74 can be formed of any suitable number of segments. The ring 74 can be attached to the periphery of the lens body 72, as discussed below with respect to the FIG. 10, or extend through a hollow edge portion of the lens body 72, as discussed below with respect to the FIG. 11. A pair of haptics 30 can be attached to the ring 74, one haptic 30 being attached to the segment 78 and the other haptic 30 being attached to the haptic so.

Referring to the FIG. 10, there is shown an enlarged cross-sectional view of the overlapping segments 76, 78 and so which form a micromotor. On the facing surfaces of the overlapping portions of the segments 76 and so are formed cooperating grooves 82. On the facing surfaces of the overlapping portions of the segments 78 and so are formed cooperating grooves 84. The grooves 82 and 84 selectively permit relative motion between the associated segments thereby fixing the power and astigmatism correction of the lens apparatus 70 at selected values as explained below.

Referring to FIG. 11, there is shown a portion of the lens apparatus 70 wherein the segments 76 and 78 overlap to form a micromotor. On the facing surfaces of the overlapping portions of the segments 76 and 78 are formed cooperating grooves 86 which selectively permit relative motion between the segments as explained below. The overlapping portions of the segments 76 and 78 slidably extend through a hollow edge portion 88 of the lens body 72.

The overlapping portions of the segments and the grooves shown in the FIGS. 10 and 11 form micromotors 90 and 92 respectively. These micromotors are representative of a plurality of such elements which can be spaced about the periphery of the lens body 72 in a manner similar to the micromotors 38 and 38' shown in the FIG. 6. The more micromotors that are used, the more uniform will be the curvature of the lens body 72 and the more precise will be the ability to adjust spherical and astigmatism correction.

Relatively little sliding movement between overlapping segments is required to change the shape of the lens body 72. One means for achieving such movement would be to form the grooves 82, 84 and 86 such that vibration of a segment at a first frequency would cause relative movement in one direction between the segments and vibration at a second frequency would cause relative movement in the opposite direction. The vibration could be induced by externally applied ultrasonic energy. Another method of achieving such movement would be to induce magnetic poles in the segments which poles would be paired to attract or repel as required. In any case, the grooves selectively permit relative motion between the associated segments thereby fixing the power and astigmatism correction of the lens apparatus 70 at selected values. External mechanical pressure on the haptics 30 could be used to trigger a micromotor to cause circumferential movement of the overlapping ridges. If the micromotor has the capability to store potential energy, then external mechanical pressure on the haptics could be utilized to release such energy or to restore such energy. For example, a compressed spring located in the positioning device 64 could be released or recompressed.

Figure 12:
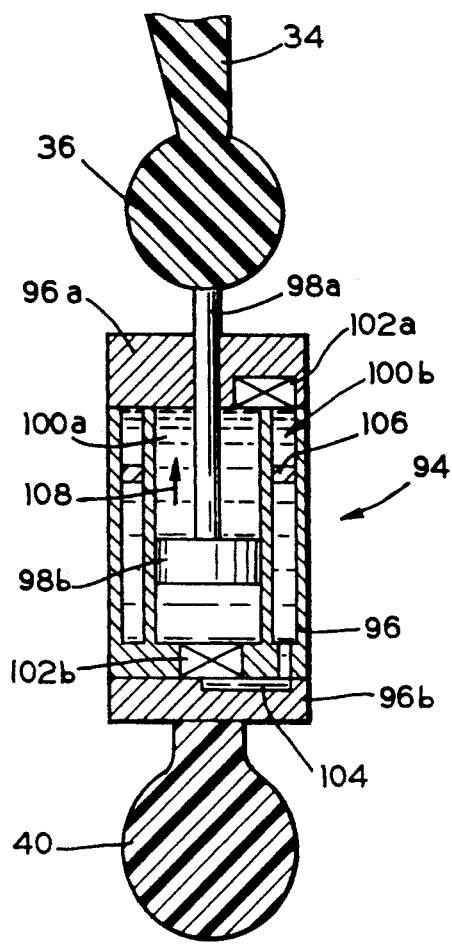
FIG. 12 is an enlarged cross-sectional view of a second alternate embodiment of a micromotor for the lens apparatus shown in the FIG. 7.

There is shown in the FIG. 12 a micromotor 94 connected between the inner ring 36 and the outer ring 40. The micromotor 94 has a central body 96 which can be generally cylindrical in shape and capped at opposite ends by a pair of end walls 96a and 96b. One end wall 96b of the body can be attached to the outer ring 40. Extending from an opposite end of the body is a rod 98a having an exposed end attached to the inner ring 36. The rod 98a extends through the end wall 96a into a cylinder chamber 100a formed in the body 96. A piston 98b is slidably retained in the chamber 100a and is attached at an upper surface to an abutting end of the rod 98a. The cylinder 100a is filled with a fluid under pressure such as a gas, the gas in an upper portion of the cylinder being at a higher pressure which forces the piston 98b toward the lower end of the cylinder 100a.

Formed concentrically about the chamber 100a is a reservoir 100b filled with a compressible fluid under pressure. The upper end of the cylinder 100a is connected to an upper end of the reservoir 100b by a two-way valve 102a located in the end wall 96b. A lower end of the cylinder 100a is connected to a lower end of the reservoir 100b by a two-way valve 102b located in the body 96 and a radially extending passageway 104 formed in the end wall 96b. The reservoir 100b is divided into upper and lower portions by an annular piston 106. The piston 106 can be responsive to a control signal such as an external source of power for actuation to move in a downward direction decreasing the pressure on the fluid in the upper portion of the reservoir 100b and increasing the pressure on the fluid in the lower portion of the reservoir 100b. Fluid will flow from the upper portion of the chamber 100a through the valve 102a into the upper portion of the reservoir 100b and fluid will flow from the lower portion of the reservoir 100b through the passageway 104 and the valve 102b into the lower portion of the chamber 100a thereby forcing the piston 98b and the rod 98a in an upward direction as indicated by an arrow 108. Movement of the piston 106 in an upward direction will cause opposite movement of the piston 98b. Such movement of the piston 98b will cause relative displacement between the inner ring 36 and the outer ring 40 thereby causing a change of shape in the lens body 34. Other forms of reservoirs could be utilized such as flexible membranes responsive to external mechanical pressure for actuating the micromotor or recharging the fluid in the reservoir thereby storing energy for later use. External mechanical pressure or external triggers such as ultrasound or laser could be utilized to actuate a micromotor or the valves 102a and 102b, or recharge a reservoir, for example by making the fluid or gas in the chamber 100a expand thereby storing energy for later use.

Figure 13:
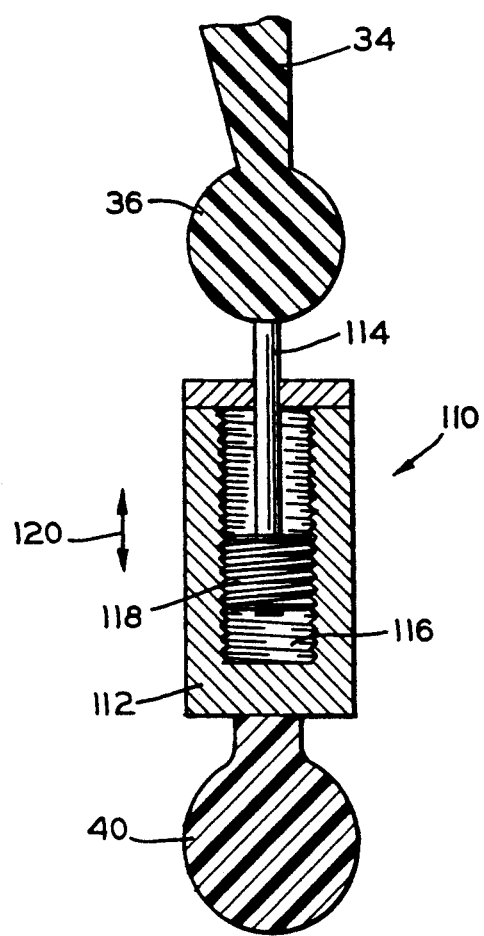
FIG. 13 is an enlarged cross-sectional view of a third alternate embodiment of a micromotor for the lens apparatus shown in the FIG. 7.

There is shown in the FIG. 13 another embodiment of the present invention. A micromotor 110 has body 112 which can be generally cylindrical and have one end attached to the outer ring 40. A rod 114 extends through an end wall of the body 112 opposite the outer ring 40. An outer end of the rod 114 is attached to the inner ring 36. An inner end of the rod 114 extends into a central cavity 116 which can be internally grooved or threaded in a helical pattern. Rotatably mounted on the rod 114 is an externally threaded nut 118 which threadably engages the wall of the cavity 116. In response to a source of external power, the nut 118 can be caused to rotate. If the nut 118 is fixed in position on the rod 114, then as the nut rotates and travels along the longitudinal axis of the cavity 116, the rod will be moved in the direction of a double headed arrow 120 to cause relative movement between the inner ring 36 and the outer ring 40 thereby changing the shape of the lens body 34.

Figure 14:
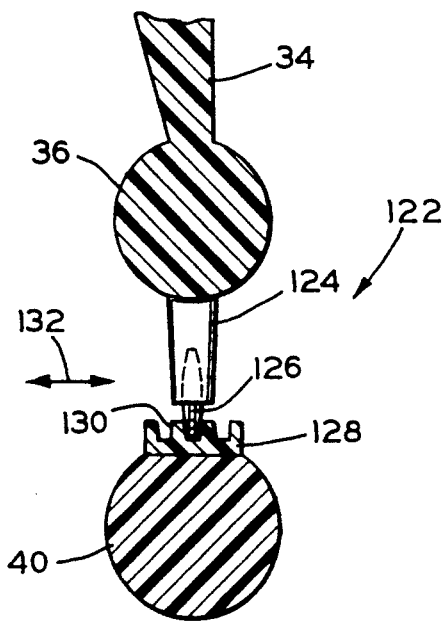
FIG. 14 is an enlarged cross-sectional view of a fourth alternate embodiment of a micromotor for the lens apparatus shown in the FIG. 7.

There is shown in the FIG. 14 yet another embodiment of the present invention. A micromotor 122 has body 124 which can be of any suitable shape with an inner end attached to the inner ring 36. The micromotor 122 also includes a motive means 126 mounted on an outer end of the body 124 adjacent the outer ring 40. An annular track 128 is attached to the inner circumference of the outer ring 40 and has an inwardly facing helical groove 130 formed therein. The motive means 126 can be any suitable device such as a wheel or endless belt which can be moved along the groove 130 to rotate the lens body 34 about its center. The motive means 126 can be driven in a conventional manner in response to a source of external power and/or control signal to rotate the lens body 34 and move the lens body in the direction of a double headed arrow 132 thereby changing the axial position and functional power of the lens body 34 when installed in an eye. The micromotor 122 is representative of a plurality of such devices which can be spaced about the inner ring 36 in a manner similar to the micromotors 38 and 38' shown in the FIG. 6.

If the groove 130 shown in the FIG. 14 is formed as a plurality of annular grooves rather than a single helical groove and the lens body 34 and the inner ring 36 are formed of a flexible material, then astigmatism correction can be made. Openings (not shown) can be formed through the walls between adjacent grooves to permit the motive means 124 to travel between the grooves. If the grooves are formed with different depths, each of the motive means 124 can be moved individually to select the desired groove thereby changing the configuration of the associated portion of the inner ring 36 and the lens body 34 to provide astigmatism correction.

The utilization of such an intraocular lens in accordance with the present invention may eliminate the need of the recovering cataract patient to wear eye glasses or contact lenses. The elimination of the glasses or contact lenses amounts to an immense benefit to the recovering cataract patient, many of whom are elderly, sometimes forgetful, and many have financial and physical hardships. Furthermore, a source of the external force can be incorporated into a pair of eyeglasses, if needed, or a hand held device to be selectively operated by the patient, or the micromotor could be responsive to pressure applied from outside the eye to produce a change in the focal length (focus) so the lens would have accommodation (the ability to change focus from distance to near). present invention has the advantage over prior art devices of not requiring a physical or electrical connection between the source of the power and the lens in order to change the lens.

The variable focus lens of the present invention has a variety of applications, in addition to the application as an intraocular lens. For example, the variable focus lens can be used as a camera lens. The lens could be used as an alternative to or in conjunction with cameras having either a fixed lens, an adjustable lens, or a plurality of interchangeable lenses.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. An adjustable focus intraocular lens apparatus, for implantation into an eye, comprising:
   a transparent lens body having a periphery which includes an expandable and contractible inner ring;
   a mounting ring positioned adjacent to said periphery of said lens body, said mounting ring including an outer ring being substantially rigid with respect to the inner ring of said lens body; and
   micrometer means coupling the outer ring of said mounting ring to the inner ring of said lens body, said micromotor means being responsive to an externally generated control signal for selectively changing at least one of the shape and the position of the inner ring of said lens body whereby when the lens apparatus is implanted into an eye and the control signal is generated outside the eye and transmitted to said micromotor means, said micromotor means responds to adjust the focus of the lens for power and astigmatism correction respectively.

2. The lens apparatus according to claim 1 wherein said micromotor means includes a linear positioning device connected between said outer ring and said inner ring.

3. An adjustable focus intraocular lens apparatus, for implantation into an eye, comprising:
   a transparent lens body having a periphery;
   an adjustable circumference inner ring attached to said periphery of said lens body;
   a plurality of micromotor means spaced about and coupled to said inner ring, and responsive to an externally generated control signal for selectively changing the circumferential length of said inner ring whereby when the lens apparatus is implanted in an eye and the control signal is generated outside the eye and transmitted to said micromotor means, said micromotor means respond to adjust the shape of the lens for power and astigmatism correction; and
   a substantially rigid outer ring, wherein each said micromotor means includes a linear positioning device connected between said outer ring and said inner ring for selectively moving said inner ring toward and away from said outer ring.

4. The lens apparatus according to claim 3 wherein said micromotor means have a source of potential energy responsive to said control signal for actuating said micromotor means and moving said inner ring with respect to said outer ring.

5. An adjustable focus intraocular lens apparatus, for implantation into an eye comprising:
   a transparent lens body having a periphery and a central axis;
   a mounting ring extending about said periphery of said lens body; and
   a plurality of micromotor means spaced equally about and attached to said mounting ring and coupled to said periphery of said lens body, each said micromotor means being responsive to an external control signal for selectively changing at least one of a circumferential length and an axial position along said central axis of an associated portion of said periphery of said lens body relative to a circumferential length and an axial position of another portion of said lens body whereby when the lens apparatus is implanted into an eye and the control signal is generated outside the eye and transmitted to said micromotor means, said micromotor means respond to adjust the lens for power and astigmatism correction.

6. The lens apparatus according to claim 5 wherein said mounting ring includes a substantially rigid outer ring, said periphery includes an expandable and contractible inner ring, each said micromotor means being attached to said outer ring and coupled to said inner ring for moving said inner ring relative to said outer ring.

7. The lens apparatus according to claim 6 wherein each said micromotor means has a body attached to one of said inner and outer rings, a piston slidably positioned in a cylinder cavity formed in said micromotor means body, and a rod connected between the other one of said inner and outer rings and said piston being responsive to a source of energy triggered by said control signal for moving said inner ring relative to said outer ring.

* * * * *